United States Patent [19]
Stern et al.

[11] Patent Number: 5,755,715
[45] Date of Patent: May 26, 1998

[54] TISSUE HEATING AND ABLATION SYSTEMS AND METHODS USING TIME-VARIABLE SET POINT TEMPERATURE CURVES FOR MONITORING AND CONTROL

[75] Inventors: Roger A. Stern, Cupertino; Dorin Panescu, Sunnyvale; David K. Swanson, Mountain View, all of Calif.

[73] Assignee: EP Technologies, Inc., San Jose, Calif.

[21] Appl. No.: 656,756

[22] Filed: Jun. 3, 1996

Related U.S. Application Data

[63] Continuation of Ser. No. 266,023, Jun. 27, 1994, abandoned, which is a continuation-in-part of Ser. No. 976,691, Nov. 13, 1992, Pat. No. 5,383,874, and a continuation-in-part of Ser. No. 72,322, Jun. 3, 1993, abandoned, which is a division of Ser. No. 37,740, Mar. 26, 1993, abandoned, which is a continuation of Ser. No. 790,578, Nov. 8, 1991, abandoned.

[51] Int. Cl.$^6$ ............................................. A61B 17/39
[52] U.S. Cl. .................................. 606/31; 606/42; 607/102
[58] Field of Search .......................... 606/27–34, 37–42, 606/45–52; 607/100–102

[56] References Cited

U.S. PATENT DOCUMENTS

| | | | |
|---|---|---|---|
| 4,860,744 | 8/1989 | Johnson et al. | 606/31 |
| 4,907,589 | 3/1990 | Cosman . | |
| 4,998,933 | 3/1991 | Eggers et al. | 606/41 |
| 5,057,105 | 10/1991 | Malone et al. | 606/31 |
| 5,122,137 | 6/1992 | Lennox | 606/49 |
| 5,180,896 | 1/1993 | Gibby et al. . | |
| 5,191,883 | 3/1993 | Lennox et al. . | |
| 5,348,554 | 9/1994 | Imran et al. | 606/41 |

*Primary Examiner*—Michael Peffley
*Attorney, Agent, or Firm*—Oppenheimer Poms Smith

[57] ABSTRACT

Systems and methods employ an energy emitting electrode to heat tissue. The systems and methods follow a prescribed temperature set curve, in which a setpoint temperature changes over time, to control the application of energy to the electrode.

21 Claims, 11 Drawing Sheets

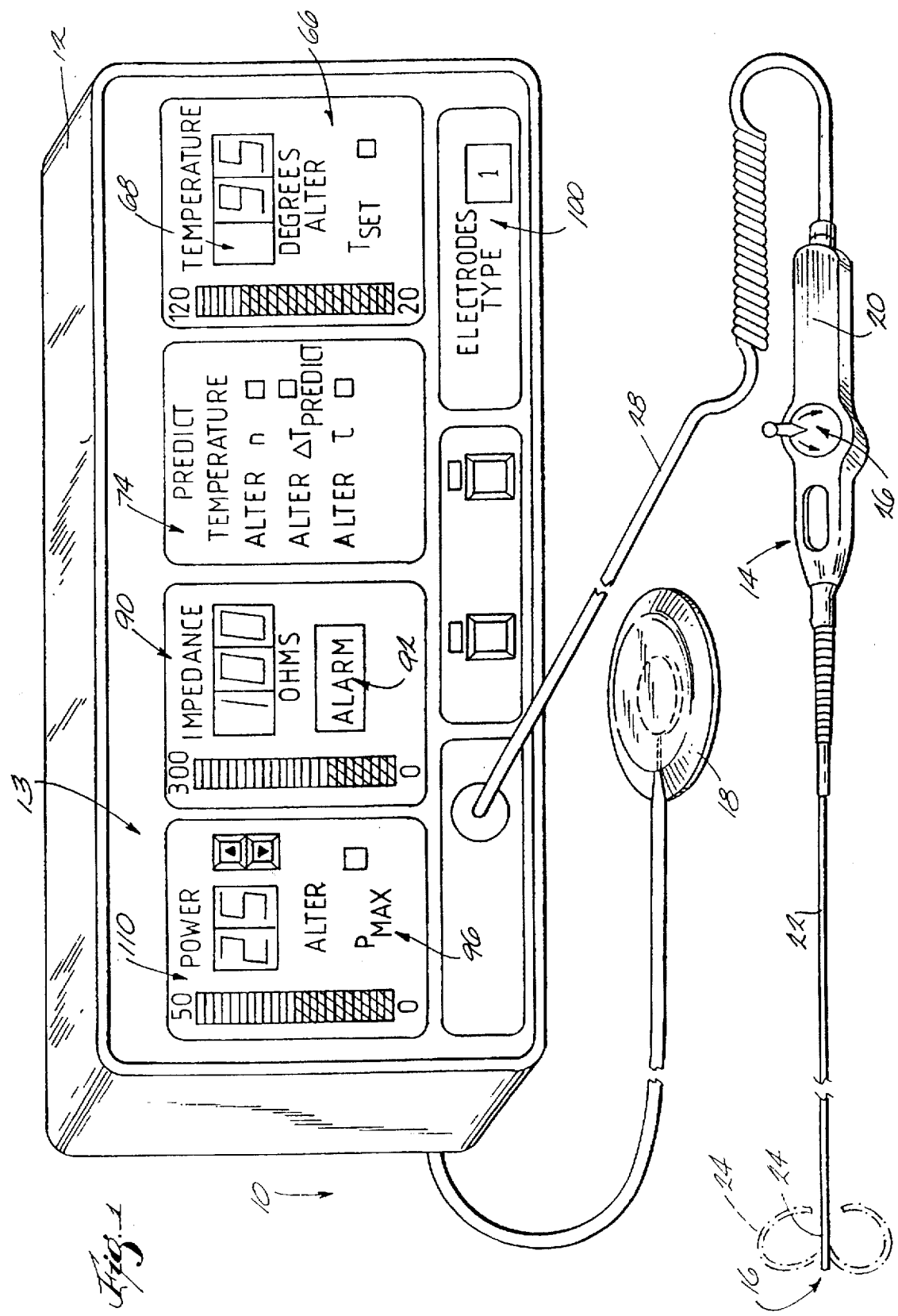

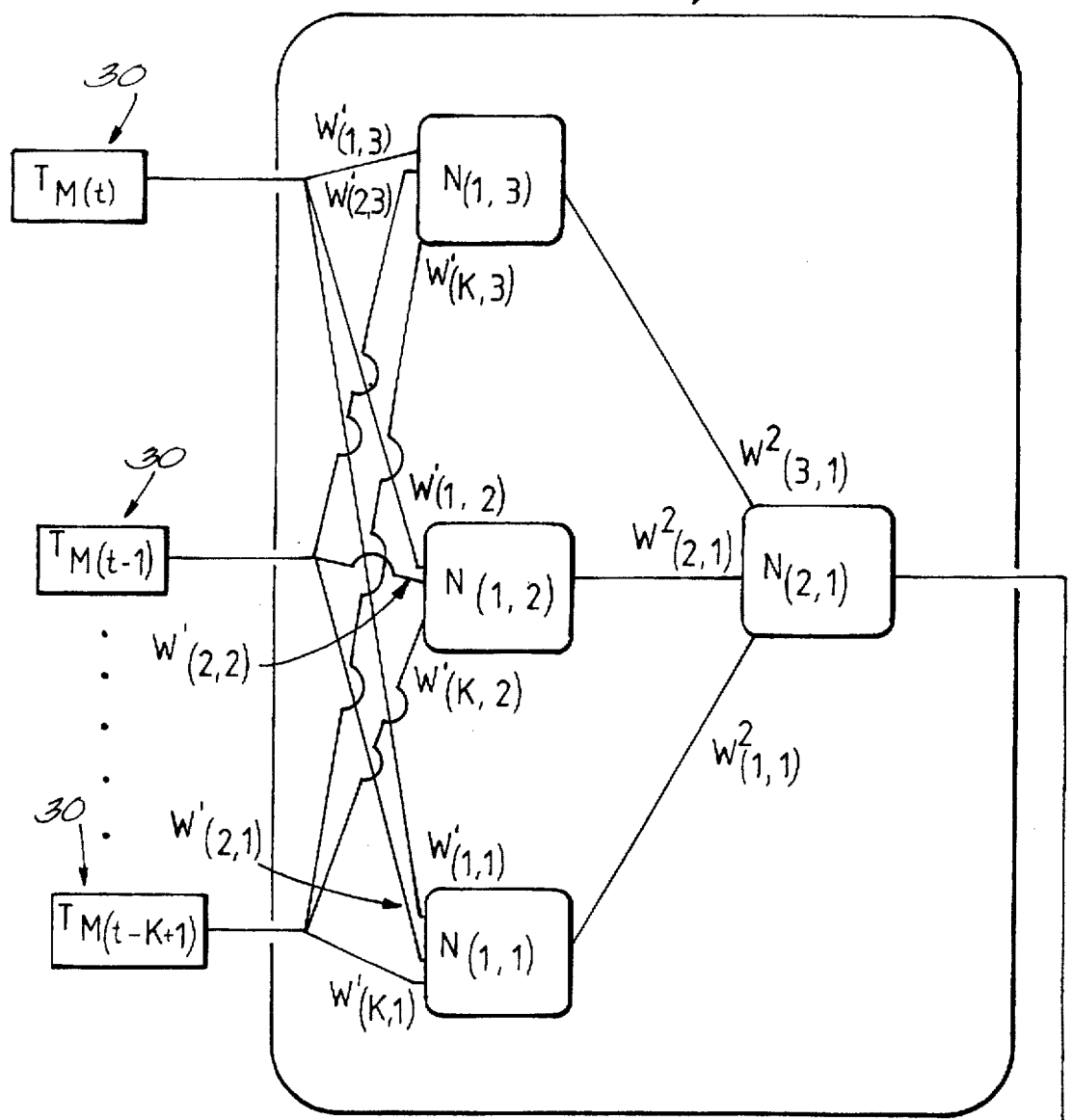
Fig. 11A
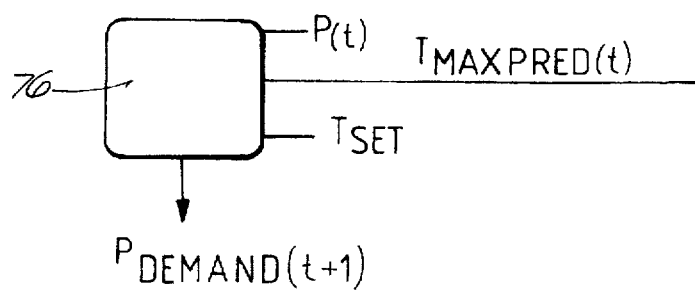

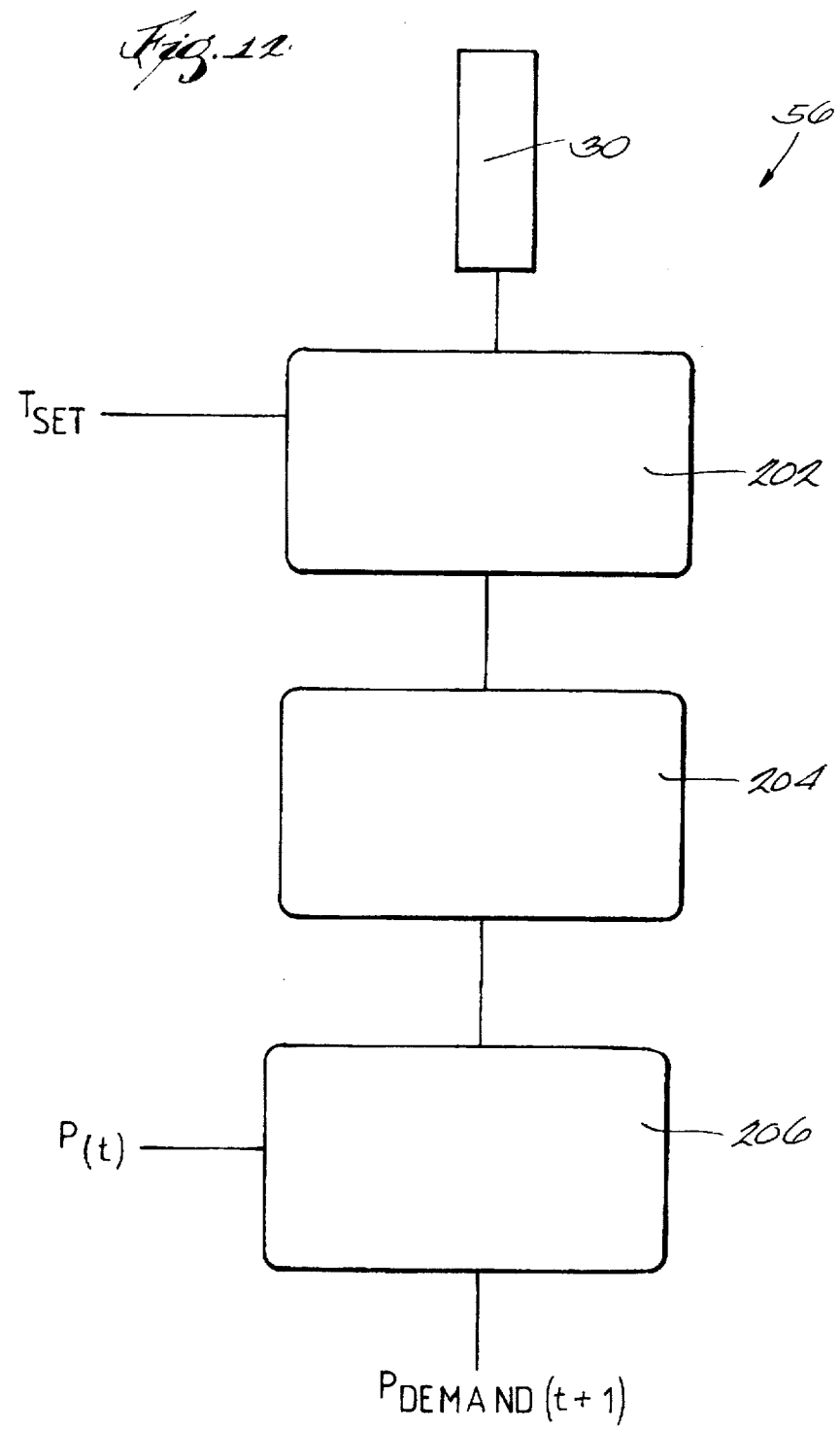

TISSUE HEATING AND ABLATION SYSTEMS AND METHODS USING TIME-VARIABLE SET POINT TEMPERATURE CURVES FOR MONITORING AND CONTROL

This is a continuation Ser. No. 08/266,023 filed on Jun. 27, 1994 (now abandoned); which is a continuation-in-part of Ser. No. 07/976,691 filed Nov. 13, 1992; now U.S. Pat. No. 5,383,874 and a continuation-in-part of Ser No. 08/072, 322 filed Jun. 3, 1993 (now abandoned); which is a Division of Ser. No. 08/037,740 filed Mar. 26, 1993 (abandoned); which is a continuation of Ser. No. 07/790,578 filed Nov. 8, 1991 (Abandoned).

FIELD OF THE INVENTION

In a general sense, the invention is directed to systems and methods for creating lesions in the interior regions of the human body. In a more particular sense, the invention is directed to systems and methods for ablating heart tissue for treating cardiac conditions.

BACKGROUND OF THE INVENTION

Physicians frequently make use of catheters today in medical procedures to gain access into interior regions of the body. In some procedures, the catheter carries an energy emitting element on its distal tip to ablate body tissues.

In such procedures, the physician must establish stable and uniform contact between the energy emitting element and the tissue to be ablated. Upon establishing contact, the physician must then carefully apply ablating energy to the element for transmission to the tissue.

The need for precise control over the emission of ablating energy is especially critical during catheter-based procedures for ablating heart tissue. These procedures, called electrophysiology therapy, are becoming increasingly more widespread for treating cardiac rhythm disturbances, called arrhythmias. Cardiac ablation procedures typically use radio frequency (RF) energy to form a lesion in heart tissue.

The principal objective of the invention is to provide systems and methods for monitoring and reliably controlling the application of energy to ablate body tissue, thereby providing therapeutic results in a consistent and predictable fashion.

SUMMARY OF THE INVENTION

The invention provides systems and methods that provide reliable control over tissue heating and ablation procedures using temperature sensing.

One aspect of the invention provides an apparatus for use in association with an energy emitting electrode for heating body tissue. The apparatus includes a memory element that stores a set temperature versus time curve for heating tissue. The curve has a first temperature value established at a first time period and a second temperature value, different than the first temperature value, established at a second time period after the first time period. The apparatus also includes a data acquisition element to derive temperature information for the energy emitting electrode at the first and second time periods. A processing element receives derived temperature information from the data acquisition element to generate (i) a first output signal based upon comparing temperature information derived at the first time period to the first temperature value and (ii) a second output signal based upon comparing temperature information derived at the second time period to the second temperature value. The apparatus includes an output element responsive to the first and/or second output signals.

In a preferred embodiment, the output element couples the electrode to a source of energy. In this embodiment, the output element includes a controller that varies the amount of energy supplied to the electrode based upon the first and/or second output signals to establish and maintain temperature at the electrode over time approximately along the temperature set curve.

Another aspect of the invention provides an apparatus and associated method for ablating body tissue. The apparatus and method establish a temperature set curve for ablating tissue, in which temperature varies over time. The apparatus and method supply ablating energy to an electrode, while deriving temperature information by sensing temperature at the electrode over time. The apparatus and method control the supply of ablating energy to the electrode based at least in part upon comparing temperature information derived at first and/or second time periods to the temperature values established by the curve over time. The apparatus and method aim to establish and maintain temperature at the electrode over time approximately along the temperature set curve.

In one embodiment, the temperature set curve includes a first region of temperature values over time that are below tissue ablating temperatures to allow thermal mapping, as well as a second region of temperature values over time that are at tissue ablating temperatures. This temperature set curve coordinates thermal mapping with tissue ablation.

In another embodiment, the temperature set curve includes a first region with a slope selected to reach tissue ablating temperatures within a prescribed time period. The temperature set curve also includes a second region of temperature values for ablating tissue, and a generally nonlinear portion between the two regions. This temperature set curve allows efficient delivery of power for ablation over relatively short time periods.

The apparatus and methods that embody the features of the invention are well suited for use in the field of cardiac ablation. They also are applicable for use in other tissue heating and ablation applications, as well. For example, the various aspects of the invention have application in procedures for ablating tissue in the prostrate, brain, gall bladder, uterus, and other regions of the body, using systems that are not necessarily catheter-based.

Other features and advantages of the inventions are set forth in the following Description and Drawings, as well as in the appended claims.

BRIEF DESCRIPTION OF THE DRAWINGS

FIG. 1 is a perspective view of a system for ablating tissue that comprises an energy emitting electrode and associated energy generator;

FIG. 12 is a schematic view of the implementation of fuzzy logic to maintain a desired set temperature condition.

Figure 3:
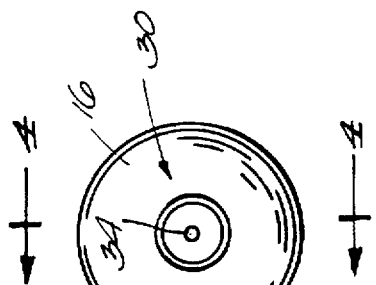
FIGS. 2, 3 and 4 are, respectively, an elevated side view, an end view, and a side section view (taken along line 4—4 in FIG. 3) of the electrode associated with the system shown in FIG. 1, the electrode having a temperature sensing element.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows a system 10 for ablating human tissue that embodies the features of the invention.

In the illustrated and preferred embodiment, the system 10 includes a generator 12 that delivers radio frequency energy to ablate tissue. Of course, other types of energy can be generated for tissue ablating purposes.

The system 10 also includes a steerable catheter 14 carrying a radio frequency emitting ablation electrode 16. In the illustrated embodiment, the ablation electrode 16 is made of platinum.

In the illustrated embodiment, the system 10 operates in a unipolar mode. In this arrangement, the system 10 includes a skin patch electrode that serves as an indifferent second electrode 18. In use, the indifferent electrode 18 attaches to the patient's back or other exterior skin area.

Alternatively, the system 10 can be operated in a bipolar mode. In this mode, the catheter 14 carries both electrodes.

The system 10 can be used in many different environments. This specification describes the system 10 when used to provide cardiac ablation therapy.

When used for this purpose, a physician steers the catheter 14 through a main vein or artery (typically the femoral vein or artery) into the interior region of the heart that is to be treated. The physician then further manipulates the catheter 14 to place the electrode 16 into contact with the tissue within the heart that is targeted for ablation. The user directs radio frequency energy from the generator 12 into the electrode 16 to ablate and form a lesion on the contacted tissue.

I. THE ABLATION CATHETER

In the embodiment shown in FIG. 1, the catheter 14 includes a handle 20, a guide tube 22, and a distal tip 24, which carries the electrode 16.

The handle 20 encloses a steering mechanism 26 for the catheter tip 24. A cable 28 extending from the rear of the handle 20 has plugs (not shown). The plugs connect the catheter 14 to the generator 12 for conveying radio frequency energy to the ablation electrode 16.

Left and right steering wires (not shown) extend through the guide tube 22 to interconnect the steering mechanism 26 to the left and right sides of the tip 24. Rotating the steering mechanism 26 to the left pulls on the left steering wire, causing the tip 24 to bend to the left. Also, rotating the steering mechanism 26 to the right pulls on the right steering wire, causing the tip 24 to bend to the right. In this way, the physician steers the ablation electrode 16 into contact with the tissue to be ablated.

Further details of this and other types of steering mechanisms for the ablating element 10 are shown in Lunquist and Thompson U.S. Pat. No. 5,254,088, which is incorporated into this Specification by reference.

A. Temperature Sensing

Figure 2:
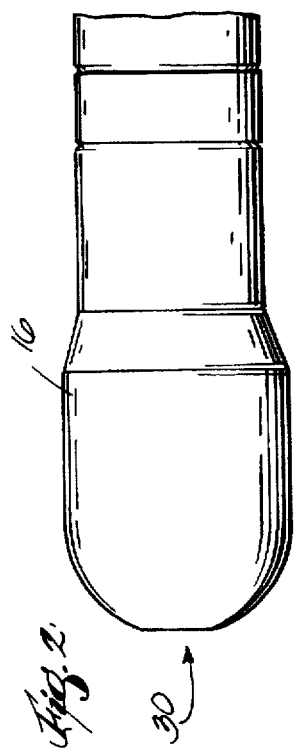
Figure 4:
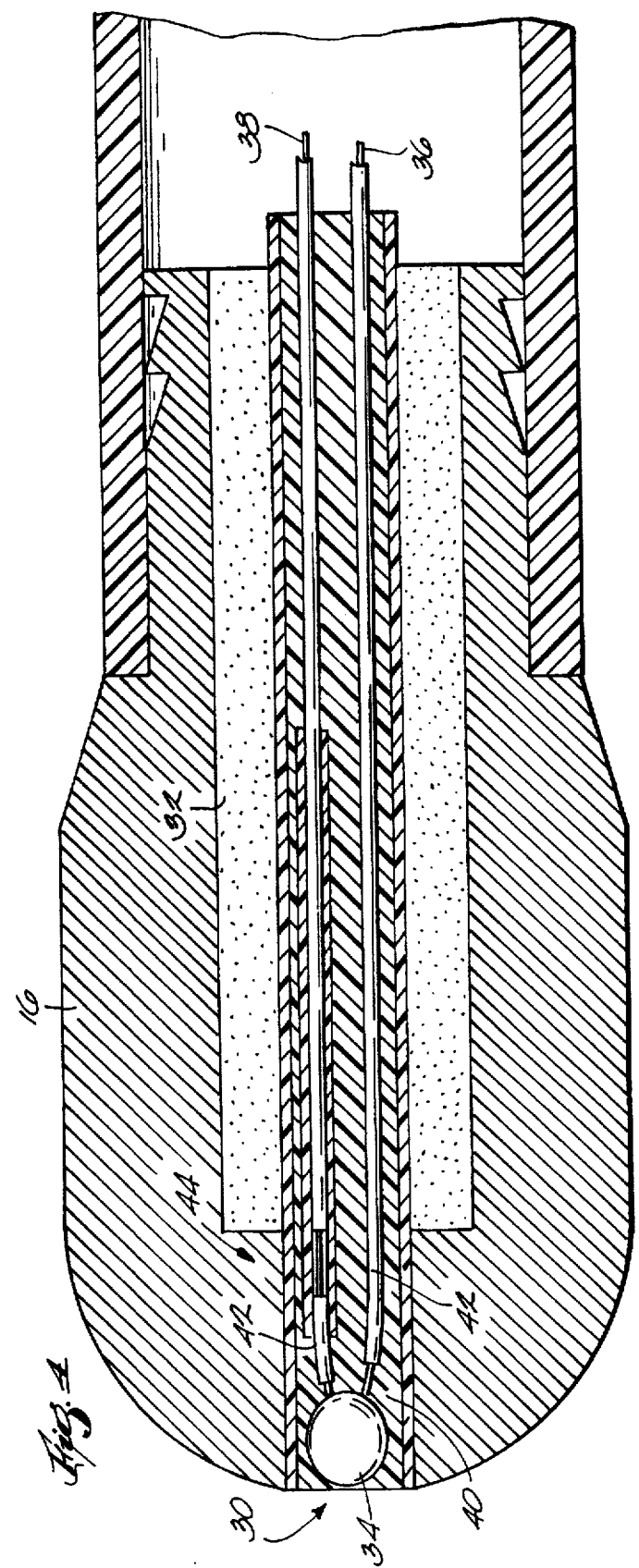

As FIGS. 2 to 4 show, the ablation electrode 16 carries at least one temperature sensing element 30. As will be described in greater detail later, the power that the generator 12 applies to the electrode 16 is set, at least in part, by the temperature conditions sensed by the element 30.

In the embodiment illustrated in FIGS. 3 to 4, the ablation electrode 16 includes an interior well 32 at its tip end. The temperature sensing element 30 occupies this well 32.

In FIGS. 3 to 4, the temperature sensing element 30 includes a small bead thermistor 34 with two associated lead wires 36 and 38. The temperature sensing tip of the thermistor 34 is exposed at the tip end of the ablation electrode 16 for tissue contact. The thermistor 34 of the type shown is commercially available from the Fenwal Co. (Massachusetts) under the trade designation 111-202CAK-BD1. The lead wires 36 and 38 comprise #36 AWG signal wire Cu+ clad steel (heavy insulation).

Potting compound 40 encapsulates the thermistor 34 and lead wires 36 and 38 within the electrode well 32. Insulating sheaths 42 also shield the encapsulated lead wires 36 and 38. Together, the compound 40 and sheaths 42 electrically insulate the thermistor 34 from the surrounding ablation electrode 16.

The potting compound 40 and insulation sheathes 42 can be made with various materials. In the illustrated embodiment, loctite adhesive serves as the potting compound 40, although another cyanoacrylate adhesive, an RTV adhesive, polyurethane, epoxy, or the like could be used. The sheathes 42 are made from polyimide material, although other conventional electrical insulating materials also can be used.

In the illustrated and preferred embodiment, a thermal insulating tube 44 envelopes the encapsulated thermistor 34 and lead wires 36 and 38. The thermal insulation tube 44 can itself be adhesively bonded to the interior wall of the well 32.

The thermal insulating material of the tube 44 can vary. In the illustrated embodiment, it is a polyimide material having a wall thickness of about 0.003 inch. Other thermal insulating materials like mylar or kapton could be used.

The lead wires 36 and 38 for the thermistor 34 extend through the guide tube 22 and into the catheter handle 20. There, the lead wires 36 and 38 electrically couple to the cable 28 extending from the handle 20. The cable 28 connects to the generator 12 and transmits the temperature signals from the thermistor 34 to the generator 12.

Figure 10:
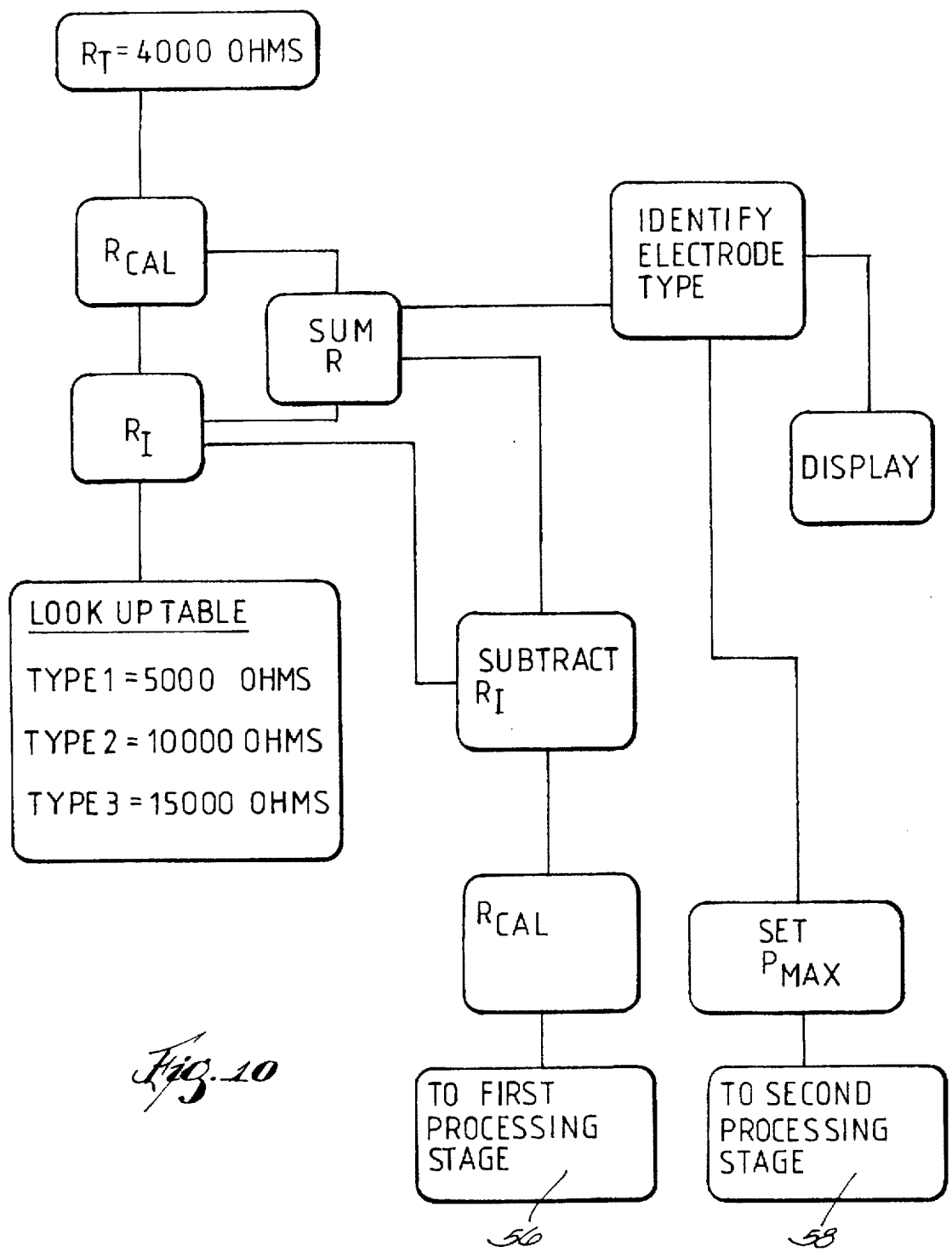
FIG. 10 is a more detailed schematic view of one of the systems shown in FIG. 9 for automatically establishing the maximum power condition based upon the physical characteristics of the ablation electrode.

In the illustrated and preferred embodiment (as FIG. 10 shows), the handle 20 carries a calibration element $R_{CAL}$ for the thermistor 34. The element $R_{CAL}$ accounts for deviations in nominal resistance among different thermistors. During manufacture of the catheter 10, the resistance of thermistor 34 is measured at a known temperature; for example, 75 degrees C. The calibration element $R_{CAL}$ has a resistance value equal to the measured value. Further details of this will be discussed later.

II. THE RF GENERATOR

Figure 5:
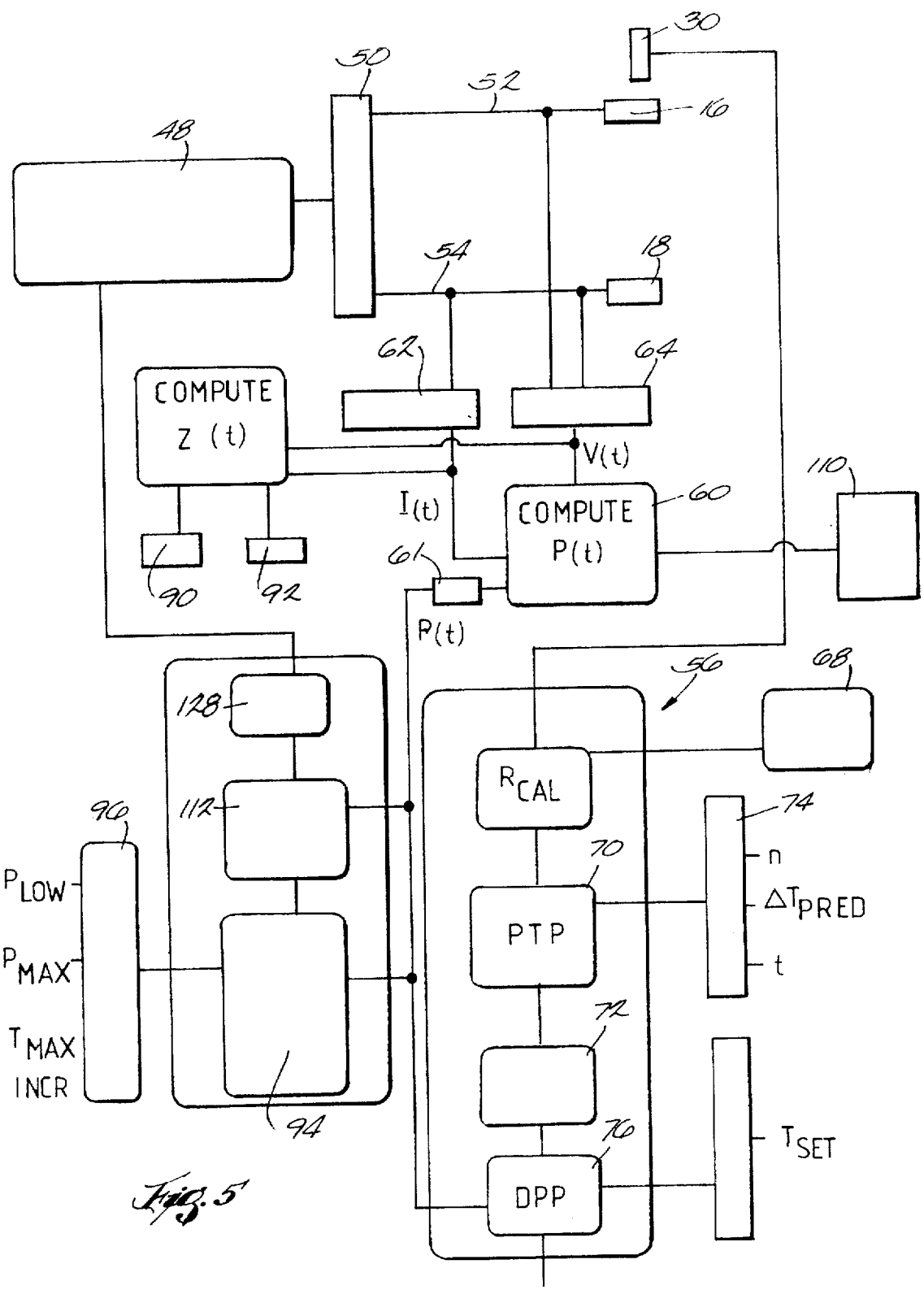
FIG. 5 is a schematic view of the generator for supplying energy to the electrode in the system shown in FIG. 1, the generator using a specialized modified PID control technique to maintain a desired set temperature by altering power in response to sensed temperature.

As FIG. 5 shows, the generator 12 includes a radio frequency power source 48 connected through a main isolation transformer 50 to outlet and return lines 52 and 54. Outlet line 52 leads to the ablation electrode 16. Return line 54 leads from the indifferent electrode 18.

In the illustrated embodiment, when used for cardiac ablation, the power source 48 is typically conditioned to deliver up to 50 watts of power at a radio frequency of 500 kHz.

The generator 12 further includes a first processing stage 56. The first processing stage 56 receives as inputs an instantaneous power signal $P_{(t)}$, a set temperature value $T_{SET}$, and a temperature control signal $T_{CONTROL}$. Analyzing these inputs using prescribed criteria, the first processing stage 56 derives a demand power signal $P_{DEMAND}$.

The generator 12 also includes a second processing stage 58. The second processing stage 58 receives as input the demand power signal $P_{DEMAND}$ from the first processing stage 56. The second processing stage 58 also receives as inputs the instantaneous power signal $P_{(t)}$ and a maximum power value $P_{MAX}$. Analyzing these inputs according to prescribed criteria, the second processing stage 58 adjusts the amplitude of the radio frequency voltage of the source, thereby adjusting the magnitude of the generated power, which $P_{(t)}$ represents.

The generator 12 preferably includes an interactive user interface 13, which is only generally shown in schematic form in FIG. 1. It should be appreciated that the interface 13 can, in conventional ways, make full use of conventional input devices (for example, a key board or mouse); output display devices (for example, a graphics display monitor or CRT); and audio and visual alarms.

A. The First Processing Stage

The generated power signal $P_{(t)}$ input for the first processing stage 56 is generated by a multiplier 60. The multiplier 60 receives an instantaneous current signal $I_{(t)}$ from an isolated current sensing transformer 62 and an instantaneous voltage signal $V_{(t)}$ from an isolated voltage sensing transformer 64.

The isolated current sensing transformer 62 is electrically coupled to the return line 54. The transformer 62 measures the instantaneous radio frequency current $I_{(t)}$ emitted by the ablation electrode 16 through body tissue to the indifferent electrode 18.

The isolated voltage sensing transformer 64 is electrically coupled between the outlet and return lines 52 and 54. The voltage sensing transformer 64 measures the instantaneous radio frequency voltage $V_{(t)}$ across body tissue between the ablation electrode 16 and the indifferent electrode 18.

The multiplier 60 multiples $I_{(t)}$ by $V_{(t)}$ to derive the instantaneous radio frequency power $P_{(t)}$, which passes through the low pass filter 61 to eliminate ripple. The filtered $P_{(t)}$ serves as the power input signal for the first processing stage 56.

In the illustrated and preferred embodiment, the generator 12 includes, as part of its overall interface 13, a display 110 (see FIG. 1 also) to show $P_{(t)}$.

The set temperature value $T_{SET}$ for the first processing stage 56 can be inputted by the physician through an interface 66, which is part of the overall interface 13 of the generator 12 (see FIG. 1 also). The set temperature value $T_{SET}$ represents the temperature the physician wants to maintain at the ablation site. The value $T_{SET}$ can be established in other ways. For example, the value $T_{SET}$ can vary over time to define a set temperature curve. Further details of this will be described later.

The set temperature value $T_{SET}$ selected depends upon the desired therapeutic characteristics of the lesion. Typical therapeutic lesion characteristics are the surface area of the tissue that is ablated and depth of the ablation. Typically, the set temperature $T_{SET}$ is in the range of 50 to 90 degrees C.

The temperature control signal $T_{CONTROL}$ input is based upon the actual instantaneous temperature conditions sensed $T_{M(t)}$ by the sensing element 30.

In the particular illustrated embodiment, the first processing stage 56 receives as $T_{CONTROL}$ the output resistance value of the thermistor 84 (in ohms). It divides this resistance value by the calibration value $R_{CAL}$ to normalize the resistance value of the thermistor 34. This normalized resistance value is the input to a read only memory (ROM) table in the generator 12, which contains stored thermistor temperature data. The ROM output is the actual measured temperature $T_{M(t)}$ (in degrees C).

The $T_{M(t)}$ output is preferably shown in a display 68, which is part of the overall interface 13 for the generator 12 (see FIG. 1 also).

The actual instantaneous temperature $T_{M(t)}$ can be used directly by the first processing stage 56. However, in the illustrated and preferred embodiment, the first processing stage 56 includes a predicted temperature processor 70 (PTP). The PTP 70 derives from $T_{M(t)}$ a predicted temperature value (designated $T_{PRED(t)}$).

(i) The Predicted Temperature Processor

The PTP 70 continuously samples $T_{M(t)}$ over prescribed sample periods $\Delta T_{SAMPLE}$. Applying prescribed criteria to these samples, the PTP 70 predicts at the end of each sample period a temperature condition $T_{PRED(t)}$ that would exist at the end of a future time period (greater than $\Delta T_{SAMPLE}$), assuming that power supplied to the ablating electrode 16 is not changed. This future time period is called the prediction period $\Delta T_{PREDICT}$.

The length of the prediction period $\Delta T_{PREDICT}$ can vary. Its maximum length depends largely upon the thermal time constant of the tissue, to take into account the expected physiological response of the tissue to temperature conditions generated during ablation. The prediction period $\Delta T_{PREDICT}$ should not exceed the time period at which the tissue can be expected to experience cellular transformation when exposed to ablating heat.

In the case of heart tissue, the thermal time constant is such that the maximum length of the prediction period $\Delta T_{PREDICT}$ should typically not exceed about two seconds. After about two seconds, cardiac tissue can be expected to begin experiencing cellular transformation when exposed to the range of temperatures generated during ablation.

$\Delta T_{SAMPLE}$ is selected to be smaller than $\Delta T_{PREDICT}$. The PTP 70 measures the instantaneous temperature $T_{M(t)}$ at the end of the present sample period and compares it to the measured temperature at the end of one or more preceding sample periods $T_{M(t-n)}$, where n is the number of preceding sample periods selected for comparison. Based upon the change in the measured temperature over time during the selected sample periods, and taking into account the relationship between the magnitude of $\Delta T_{SAMPLE}$ and $\Delta T_{PREDICT}$, the PTP 70 predicts $T_{PRED(t)}$ as follows:

$$T_{PRED(t)} = T_{M(t)} \left( \frac{i+K}{i} \right) - T_{M(t-i)} \left( \frac{K}{i} \right)$$

where:

$$K = \frac{\Delta T_{PREDICT}}{\Delta T_{SAMPLE}}$$

and i=1 to n.

In a representative implementation of the PTP 70 for cardiac ablation, $\Delta T_{PREDICT}$ is selected to be 0.48 second, and $\Delta T_{SAMPLE}$ is selected to be 0.02 second (a sampling rate of 50 Hz). Therefore, in this implementation, K=24.

Furthermore, in this implementation, n is selected to be 1. That is, the PTP 70 takes into account $T_{M(t)}$ for the instant sample period (t) and $T_{M(t-1)}$ for the preceding sample period (t-1).

In this implementation, the PTP 70 derives $T_{PRED(t)}$ as follows:

$$T_{PRED(t)} = 25 T_{M(t)} - 24 t_{M(t-)}$$

In the illustrated and preferred embodiment, the PTP 70 includes a low pass filter 72 with a selected time constant ($\tau$). The PTP 70 averages $T_{PRED(t)}$ through the filter 72 before supplying it to a demand power processor DPP 76, which will be described later.

The time constant ($\tau$) of the filter 72 selected can vary, according to the degree of accuracy desired. Generally speaking, a mid-range time constant ($\tau$) of about 0.2 second to about 0.7 second will provide the required accuracy. In the above described representative implementation, a time constant ($\tau$) of 0.25 second is used.

The degree of accuracy of the PTP 70 can also be altered by varying K. More particularly, by lowering the value of K, one can expect the PTP 70 to achieve a greater degree of accuracy in predicting the future temperature $T_{PRED(t)}$. The value of K can be varied by selecting values for $\Delta T_{SAMPLE}$ or $\Delta T_{PREDICT}$, or both. Preferably, the value of K is varied by selecting $\Delta T_{PREDICT}$.

The degree of accuracy PTP 70 can also be improved, if desired, by selecting greater values for n; that is, by taking into account more past values of $T_{M(t)}$ in calculating $T_{PRED(t)}$.

In the illustrated and preferred embodiment, the PTP 70 includes a user interface 74, which is part of the overall interface 13 of the generator 12 (see FIG. 1 also). Using the interface 74, the physician can select and modify the sampling history (n); the prediction period $\Delta T_{PREDICT}$; and the time constant (T) in real time, on line.

As will be described in greater detail later, the ability to vary the accuracy of the PTP 70 in calculating $T_{PRED(t)}$ with on line changes provides flexibility in adapting the first processing stage 56 to differing ablating conditions.

(ii) The Demand Power Processor (DPP)

The first processing stage 56 further includes a demand power processor (DPP) 76. The DPP 76 periodically compares $T_{PRED(t)}$ to the set temperature value $T_{SET}$. Based upon this comparison, and taking into account the magnitude of the instantaneous power $P_{(t)}$ supplied to the ablating electrode 16, the DPP 76 derives the demand power output $P_{DEMAND}$. The DPP 76 also takes into account other system operating goals and criteria, like response time, steady state temperature error, and maximum temperature overshoot.

The demand power output $P_{DEMAND}$ of the first processing stage 56 represents the magnitude of the radio frequency power that should be supplied to the ablating electrode 16 to establish or maintain the desired local temperature condition $T_{SET}$ at the ablating electrode 16.

The manner in which the DPP 76 derives $P_{DEMAND}$ can vary. For example, it can employ proportional control principles, proportional integral derivative (PID) control principles, adaptive control, neural network, and fuzzy logic control principles.

(a) Modified PID Control Using Fixed $T_{SET}$

In the illustrated and preferred embodiment, the DPP 76 employs a modified velocity PID control technique specially adapted for cardiac ablation. Using this technique, the DPP 76 controls the magnitude of $P_{DEMAND}$ based upon a fixed value of $T_{SET}$ established by the physician.

In the preferred and illustrated implementation, the DPP 76 compares a derived operating value $V_D$ to a preselected set value ($V_S$) for the operating condition. The DPP 76 establishes an error signal ($\Delta$) based upon the comparison, where:

$$\Delta = V_S - V_D$$

The DPP 76 issues the power demand signal for the next time period $P_{DEMAND(t+1)}$ based upon a non-linear function of the present and past values of the error signal $\Delta$, i.e.:

$$P_{DEMAND(t+1)} = f(\Delta_1, \Delta_2, \Delta_3, \ldots, \Delta_N)$$

In the general sense, f is a N-variable nonlinear function that the DPP 76 follows in performing its processing function. $\Delta_1, \Delta_2, \Delta_3, \ldots, \Delta_N$ are the values of the error signal $\Delta$ at N different moments of time. The DPP 76 thereby adjusts the power by an increment based upon a nonlinear function of the present and past values of the error signal $\Delta$.

More particularly, in the illustrated and preferred implementation, at the end of each sample period (t), the DPP 76 derives the demand power output required for the next sample period (t+1), as follows:

$$P_{DEMAND(t+1)} = P_{(t)} + S[\alpha E_{(t)} - \beta E_{(t-1)} + \delta E_{(t-2)}]$$

where the nonlinear function $f(\Delta)$ is expressed as:

$$f(\Delta) = S[\alpha E_{(t)} - \beta E_{(t-1)} + \delta E_{(t-2)}]$$

the error signal $\Delta$ is expressed as $E_{(t)}$, where $V_D$ is $T_{PRED}$ and $V_S$ is $T_{SET}$, so that $E_{(t)} = T_{SET} - T_{PRED(t)}$. In this implementation, a threshold value of $T_{SET}$ is selected, which remains essentially constant as $T_{PRED(t)}$ is determined by the PTP 70, and $\alpha$, $\beta$, and $\delta$ are conventional velocity PID expressions based upon a proportional constant $K_p$ (relating to the magnitude of the difference); an integral constant $K_i$ (relating to the change in the difference over time); and a derivative constant $K_d$ (relating to rate at which the difference is changing over time); and $\Delta T_{SAMPLE}$, as follows:

$$\alpha = K_p + \frac{K_i \Delta T_{SAMPLE}}{2} + \frac{K_d}{\Delta T_{SAMPLE}}$$

$$\beta = \frac{K_i \Delta T_{SAMPLE}}{2} - K_p - \frac{2K_d}{\Delta T_{SAMPLE}}$$

$$\delta = \frac{K_d}{\Delta T_{SAMPLE}}$$

and and S is a selected scaling factor, whose value depends upon whether $T_{PRED(t)}$ is greater than or less than $T_{SET}$, as follows:

S=X when $E_{(t)}>0$ (i.e., $T_{SET}>T_{PRED(t)}$).
S=Y when $E_{(t)}<0$ (i.e., $T_{SET}<T_{PRED(t)}$), and
The value of S is asymmetric; that is, X is different than Y and, most preferably, Y>X.

The above relationships assume that the desired error $E_{(t)}$ to be maintained is zero. Other desired error values could be used. Using the asymmetric scaling factor S provides the desired nonlinear response $f(\Delta)$ over time to maintain the desired error $E_{(t)}$. In maintaining the desired error at zero, the $f(\Delta)$ of the DPP 76 decreases power faster (when $T_{PRED(t)}>T_{SET}$) than increasing power (when $T_{PRED(t)}<T_{SET}$).

In the illustrated and preferred embodiment, the DPP 76 uses fixed values for the coefficients $K_p$, $K_i$, and $K_d$, regardless of the particular ablating conditions.

The calculation for $P_{DEMAND}$ can be adapted on line by the physician to changing ablating conditions encountered, by adjusting the front end calculation of $T_{PRED(t)}$ by the PTP 70. Because of the flexibility to make on line adjustments that the PTP 70 provides, multiple value tables of $K_p$, $K_i$, and $K_d$ are not necessary in the system to accommodate changes in ablating conditions.

Applicants have determined that the following values of for $K_p$, $K_i$, and $K_d$ can be used in the DPP 76:

$K_p = 0.025375$ $K_i = 97.0695$ $K_d = 7.82 \times 10^{-5}$

In a representative implementation of the DPP 76, $\Delta T_{SAMPLE} = 0.02$, and therefore $\alpha = 0.99998$ $\beta = 0.93750$ $\delta = 3.91 \times 10^{-3}$.

In this representative implementation of the DPP 76,

S=2.0 when $E_{(t)}>0$ (i.e., $T_{SET}>T_{PRED(t)}$), and

S=8.0 when $E_{(t)}<0$ (i.e., $T_{SET}<T_{PRED}$).

This representative implementation adjusts $P_{DEMAND(t)}$ to reach $T_{SET} \pm 3°$ C. within 5.0 seconds, if not limited by available power. It also aims to keep a peak steady state temperature error (defined as $T_{SET}-T_{PRED(t)}$) of less than 3° C. The implementation also adjusts $P_{DEMAND(t)}$ over time to avoid overshooting $T_{SET}$ by more than 3° C.

(b) Modified PID Control Using Variable $T_{SET}$

In an alternative embodiment, the DPP 76 uses modified velocity PID control described above to control the magnitude of $P_{DEMAND}$ based upon varying values of $T_{SET}$ over time. In this embodiment, $T_{SET}$ is expressed as a function with respect to time (see FIGS. 6A and 6B), which can be linear or nonlinear or both. In this embodiment, $T_{SET}$ comprises a temperature versus time curve (see FIGS. 6A and 6B) for heating tissue. The curve has a first temperature value set at a first time period and at least one additional temperature value, different than the first temperature value, set at a second time period after the first time period.

Figure 6A:
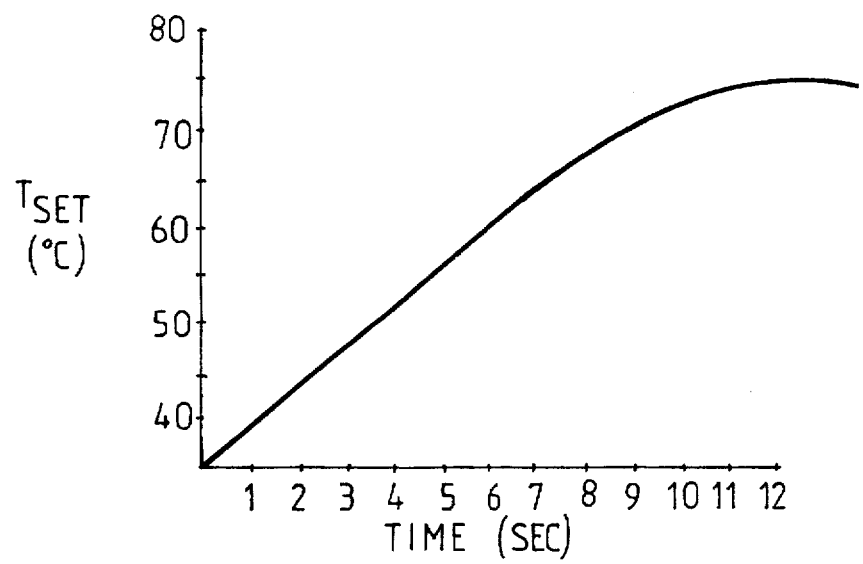
FIGS. 6A and 6B are graphs showing curves of set temperature conditions for the generator to maintain over time.

As FIG. 6A shows, $T_{SET}$ can be expressed in terms of a linear function at the outset of the ablation procedure (for example, during the first 5 seconds). From t=0 to t=5 seconds, the value of $T_{SET}$ progressively increases as a straight line with a selected slope. At t=6 seconds, $T_{SET}$ begins to be expressed in term of a nonlinear function, so that the slope flattens out as $T_{SET}$ approaches a preselected final control value for ablation.

Figure 6B:
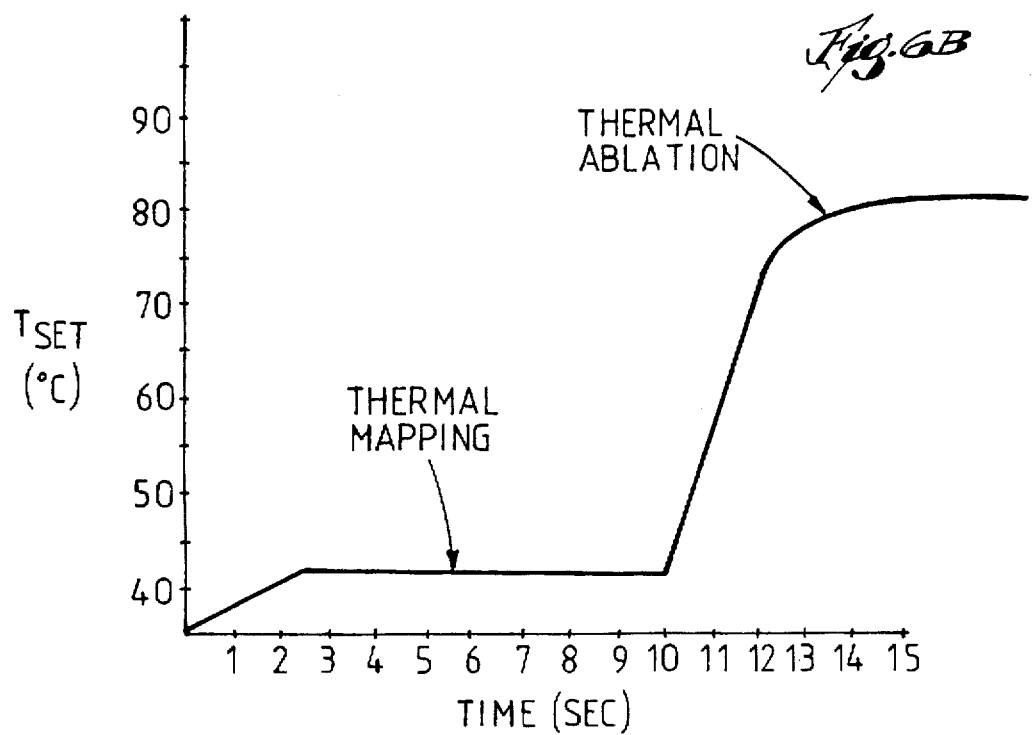

In an alternative implementation (shown in FIG. 6B), the $T_{SET}$ defines a complex curve to accommodate thermal mapping before thermal ablation. As FIG. 6B shows, from t=0 to t=2 seconds, the value of $T_{SET}$ progressively increases as a straight line with a selected slope. At t=3 seconds, $T_{SET}$ begins to be expressed in term of a nonlinear function, and the slope flattens out as $T_{SET}$ approaches a first preselected value for thermal mapping. The slope remains flat until t=10, when the value of $T_{SET}$ again progressively increases as a straight line with a selected slope. At t=13 seconds, $T_{SET}$ again begins to be expressed in term of a nonlinear function, and the slope flattens out as $T_{SET}$ approaches a second preselected value for tissue ablation. In the example shown in FIG. 6B, the first value of $T_{SET}$ for thermal mapping is within 45° C. to 50° C., whereas the second value for $T_{SET}$ for tissue ablation is within 50° C. to 90° C., and preferable about 70° C. Moreover, $T_{SET}$ can be defined as a true function of time.

In either implementation FIG. 6A or 6B, the DPP 76 receives as input changing values of $T_{SET}$ over time, which define the prescribed set temperature curve. The system calculates $E_{(t)}$ based upon these changing values to derive $P_{DEMAND}$, in the same manner that the system derives $P_{DEMAND}$ based upon a constant value of $T_{SET}$.

(c) Adaptive Control System

Figure 7:
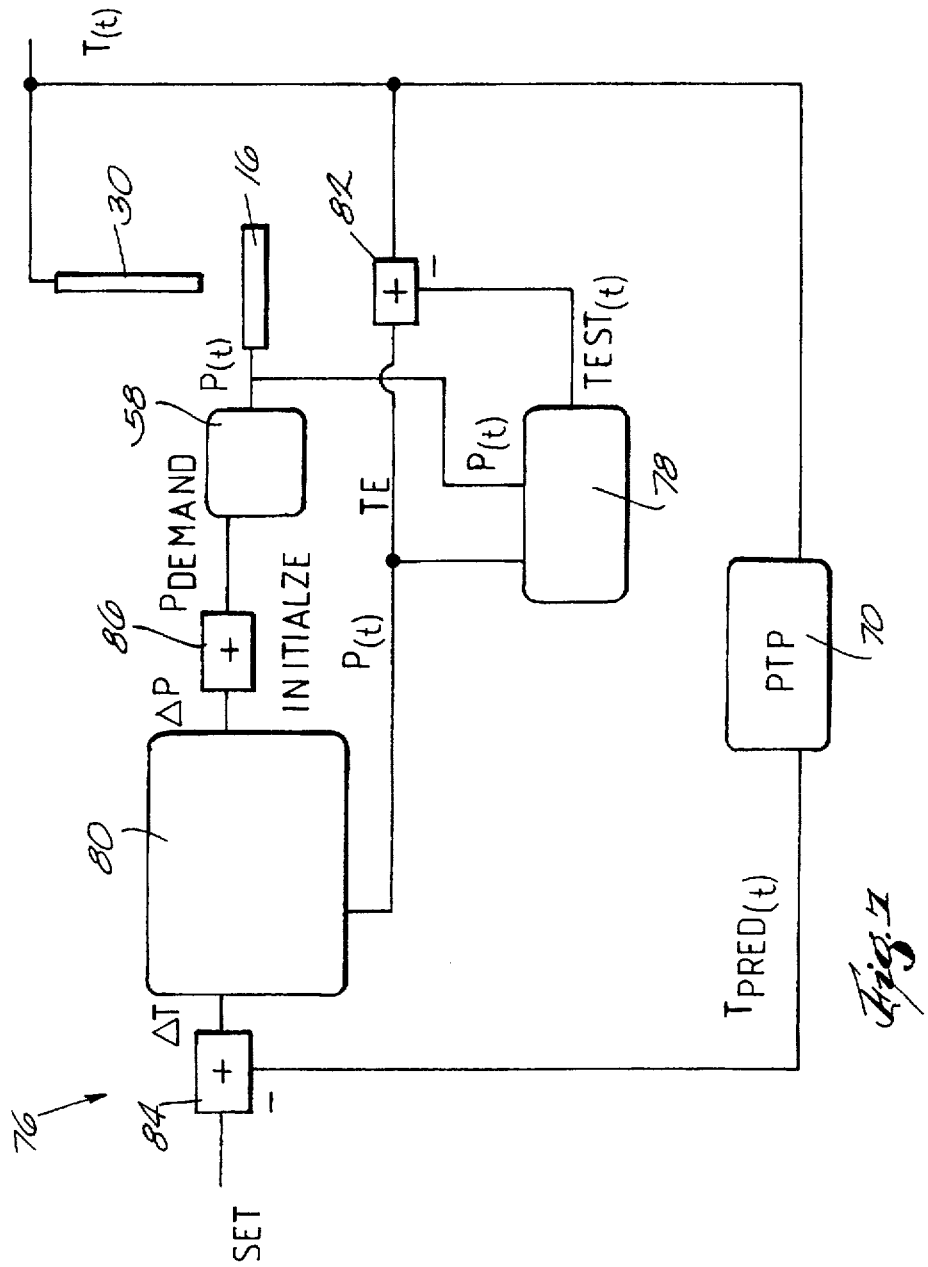
FIG. 7 is a schematic view of an alternative system for use in association with the generator shown in FIG. 5 to alter applied power in response to sensed temperature, using adaptive control techniques.

FIG. 7 shows an alternative implantation of the DPP 76, which derives $P_{DEMAND}$ using adaptive control principles. In this implementation, the DPP 76 receives as input $T_{SET}$ and $T_{PRED}$ in the manner previously described. The values of $T_{SET}$ can be fixed or can vary with time, as also previously described.

In the implementation shown in FIG. 7, the DPP 76 further includes a pair of adaptive filters 78 and 80. Each filter 78 and 80 generates an output based upon an input, expressed in terms of an assumed relationship between them. In the illustrated implementation, the output comprises an estimate, based upon the assumed relationship, of an external condition that can be independently measured by the DPP 76. The DPP 76 compares the estimated output to the actually measured external condition and adjusts the coefficients of the assumed relationship to minimize the error between the two.

In the implementation of the DPP 76 shown in FIG. 7, the filter 78 receives as input the instantaneous power $P_{(t)}$ applied by the RF source 48 to the ablating electrode 16. The filter 78 generates as output an estimate of the temperature condition $T_{EST(t)}$ that the sensing element 30 should sense, given $P_{(t)}$ and the assumed relationship between $P_{(t)}$ and the temperature $T_{(t)}$ at the ablation site. The filter 78 therefore approximates the heat transfer function of the tissue contacting the ablating electrode 16.

The DPP 76 includes a summing junction 82, which derives a temperature error signal $T_E$ by subtracting the estimated temperature $T_{EST(t)}$ from the temperature $T_{(t)}$ actually sensed by the sensing element 30. The DPP 76 feeds back the error signal TE to the filter 78. The filter 78 adjusts the coefficients of the assumed relationship between $P_{(t)}$ and $T_{(t)}$ to minimize the magnitude of the error $T_E$.

In a preferred implementation, the filter 78 uses a finite linear sequence to express the assumed relationship between $P_{(t)}$ and $T_{(t)}$. The sequence estimates a future temperature $T_{EST(t+1)}$ based upon present instantaneous power $P_{(t)}$ and the past power $P_{(t-n)}$, where n represents the number of past power conditions taken into account. The quantity n can vary according to the accuracy desired.

In an illustrative implementation, the filter 78 takes into account the present power $P_{(t)}$ and the preceding power $P_{(t-1)}$ (i.e., n=1). In this implementation, the finite linear sequence is expressed as follows:

$$T_{EST(t+1)} = aP_{(t)} + bP_{(t-1)}$$

where a and b represent the assumed transfer coefficients.

The assumed transfer coefficients comprise initially selected values which are then adjusted to minimize the error signal $T_E$. This adaptive adjustment can be accomplished using various known techniques. For example, the coefficients can be adjusted based upon the Least Mean Square (LMS) method, which tends to minimize the square of the error $T_E$.

The LMS method updates the coefficients a and b, as follows:

$$T_{E(t)} = T_{(t)} - T_{EST(t)}$$

$$a_{(t+1)} = a_{(t)} + \mu P_{(t)} T_{E(t)}$$

$$b_{(t+1)} = b_{(t)} + \mu P_{(t-1)} T_{E(t)}$$

where μ is the step-size of the algorithm.

A larger μ provides a faster convergence rate but a larger ripple about the optimal coefficients. A smaller μ reduces both the convergence rate and the ripple about the optimal solution. The optimal value of μ depends on the characteristics of the system to be modeled. In the case of the illustrated electrode-blood-tissue system, μ lies in the interval between 0.01 and 0.5.

The filter 80 is the inverse of the filter 78. The filter 80 receives as input a temperature error signal ΔT generated by the summing junction 84. The summing junction 84 subtracts $T_{PREDICT(t)}$ from $T_{SET}$ to generate the error signal ΔT.

The filter 80 generates as output ΔP, which represents an approximation of how much the power $P_{(t)}$ should be altered in view of ΔT, based upon the inverse of the assumed relationship between power $P_{(t)}$ and temperature $T_{(t)}$ that the filter 78 uses. In the context of the assumed relationship given for the filter 78, the relationship used by the filter 80 can be approximated using a second order Taylor series, as follows:

$$\Delta P_{(t)} = \frac{1}{a} \Delta T_{(t)} - \frac{b}{a^2} \Delta T_{(t-1)} + \frac{2b^2}{a^3} \Delta T_{(t-2)}$$

The filter 80 adjusts its coefficients in relation to the adjustments made by the filter 78 to the coefficients a and b, based upon the error signal $T_E$ of the summing junction 82, to minimize the magnitude of this error signal $T_E$.

The output ΔP of the filter 80 is fed through another summing junction 86, which is initialized at the outset of the ablation procedure at the beginning power level $P_0$. The summing junction 86 continuously adjusts the beginning power value with the ΔP output of the inverse filter 80. The output of the summing junction 86 therefore comprises $P_{DEMAND}$.

The DPP 76 shown in FIG. 7 sends the output $P_{DEMAND}$ to the second processing stage 58 to modify $P_{(t)}$.

(d) Neural Network Prediction Control Because of the particular heat exchange conditions between the tissue and the metallic ablation electrode 16 contacting it, the temperatures measured by the sensing element 30 may not correspond exactly with the actual maximum tissue temperature. This is because the region of hottest temperature occurs beneath the surface of the tissue at a depth of about 0.5 to 1.0 mm from where the energy emitting electrode 16 (and the sensing element 30) contacts the tissue. If the power is applied to heat the tissue too quickly, the actual maximum tissue temperature in this region may exceed 100° C. and lead to tissue desiccation.

FIG. 11A shows an alternative embodiment of the DPP 76 which derives $P_{DEMAND}$ using neural network control principles. In this implementation, the PTP 70 receives as input a predicted temperature of the hottest tissue region $T_{MAXPRED(t)}$ from a neural network predictor 200. The DPP 76 derives $P_{DEMAND(t+1)}$ based upon the difference between this $T_{MAXPREDICT(t)}$ and $T_{SET}$. The values of $T_{SET}$ can be fixed, or they can vary with time, as previously described.

In this implementation, the predictor 200 comprises a two-layer neural network, although more hidden layers could be used. The predictor 200 receives as inputs a set of k past samples of temperatures sensed by the element 30 $(T_{M(t-k+1)})$. For example, to cover the past two seconds at a sampling period of 0.02 second, k=100.

The predictor 200 includes a first and second hidden layers and four neurons, designated $N_{(L,x)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

The weighted past samples of the sensing element 30 $T_{M(t-i+1)}$ (i=1 to k) are fed as inputs to each neuron $N_{(1,1)}$; $N_{(1,2)}$; and $N_{(1,3)}$ of the first layer. FIG. 11 represents the weighted input samples as $W^L_{(k,N)}$, where L=1; k is the sample order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 11 represents the weighted outputs as $W^L_{(O,X)}$, where L=2; O is the output neuron 1, 2, or 3 of the first layer; and X is the input neuron number 1 of the second layer. Based upon these weighted inputs, the output neuron $N_{(2,1)}$ predicts $T_{MAXPRED(t)}$.

The predictor 200 must be trained on a known set of data that have been previously acquired experimentally. For example, using a backpropagation model, the predictor 200 can be trained to predict the known hottest temperature of the data set with the least error. Once the training phase is completed, the predictor 200 can be used to predict $T_{MAXPRED(t)}$.

Figure 11B:
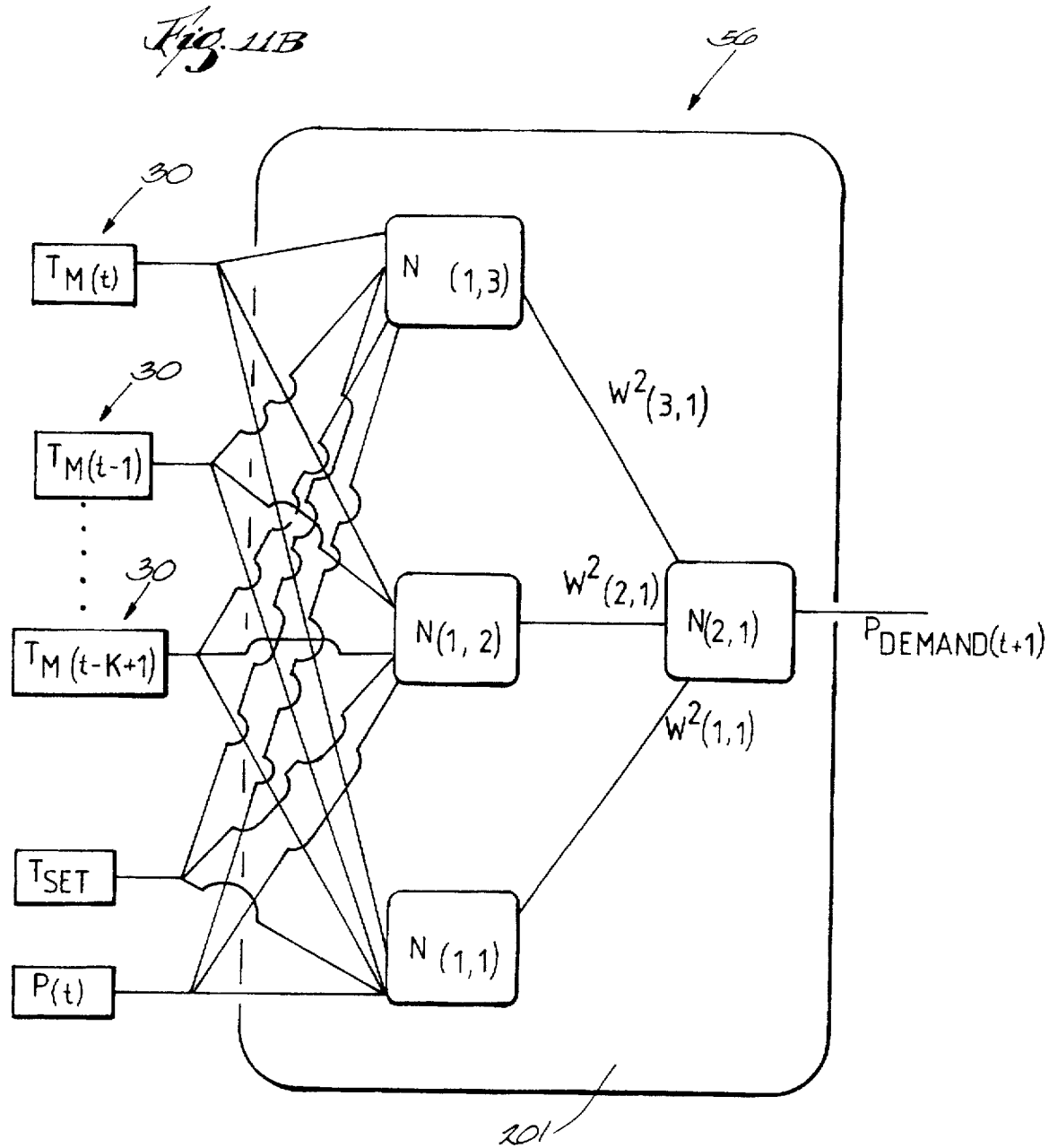
FIGS. 11A and B are schematic views of the implementation of a neural network predictor to maintain a desired set temperature by altering power in response to a prediction of maximum tissue temperature.

As FIG. 11B shows, the first processing stage 56 can use a single neural network 201 to derive $P_{DEMAND(t)}$. In this implementation, the network 201 receive as input, in addition to k past samples of temperatures from the sensor 30, the value of $T_{SET}$, and the current power $P_{(t)}$. The network 201 derives $P_{DEMAND(t)}$ as output, which reflects the power level required to keep the hottest predicted temperature at or about $T_{SET}$. As before stated, a set of data containing a solution based upon all the desired inputs is necessary to train the neural network of the predictor 201 to manipulate the input and obtain the desired output with the least amount of error.

(e) Fuzzy Logic Control

FIG. 12 shows an alternative embodiment of the first processing stage 56 which derives $P_{DEMAND}$ using fuzzy logic control principles. In this implementation, the first processing stage 56 includes a fuzzifier 202, which receives as inputs the temperature signals $T_{M(t)}$ from the sensor 30. The fuzzifier 202 also receives $T_{SET}$ as input, either as a constant value or a value that changes over time. The fuzzifier 202 converts the $T_{M(t)}$ input data to fuzzy inputs based upon reference to $T_{SET}$ on a relative basis. For example, the fuzzy inputs can determine the degree (or membership function) to which a given $T_{M(t)}$ is, compared to $T_{SET}$, "cool" or "warm" or "warmer" or "hot".

These fuzzy inputs are passed through an I/O mapper 204 which converts them to fuzzy outputs by translating the inputs into descriptive labels of power. This is accomplished, for example, by using linguistic "if . . . then" rules, like "if the fuzzy input is . . . then the fuzzy output is . . . ." Alternatively, more complex mapping matricial operators can be used.

For example, if $T_{M(t)}$ is "cool," the I/O mapper 204 outputs the descriptive label "Largest Positive," to indicate that a large relative increase in power is required. By the same token, if $T_{M(t)}$ is "hot," the I/O mapper 204 outputs the descriptive label "Largest Negative," to indicate that large relative decrease in power is required. The intermediate fuzzy inputs "warm" and "warmer" produce intermediate descriptive labels as fuzzy outputs, such as "Smallest Positive" and "Smallest Negative."

These fuzzy outputs are passed through a defuzzifier 206. The defuzzifier 206 also receives actual power $P_{(t)}$ as an input, since the fuzzy outputs refer to variations in $P_{(t)}$. Based upon $P_{(t)}$ and the variations required based upon the fuzzy outputs, the defuzzifier 206 derives $P_{DEMAND(t)}$.

To finely trim the reference sets and the rules of the I/O mapper 204, it may be required that the fuzzy logic controller be trained on a known set of data before use.

B. The Second Processing Stage

In the illustrated and preferred embodiment, the second processing stage 58 (see FIG. 5) includes a converter 112. The converter 112 derives a command voltage signal $V_{DEMAND(t)}$ based upon a power input signal to adjust the amplitude of the voltage $V_{(t)}$ supplied to the source 48 to thereby adjust $P_{(t)}$. Alternatively, the converter 112 could derive a command current signal $I_{DEMAND(t)}$ based upon a power input signal to adjust the amplitude of the current supplied to the source 48, achieving the same results.

(i) The Power Down Stage

In one implementation, the power input to the converter 112 could comprise $P_{DEMAND(t)}$ as derived by the DPP 76. In the illustrated and preferred embodiment, the second processing stage 58 includes a demand power down stage 94 between the DPP 76 and the converter 112. The power down stage 94 receives $P_{DEMAND(t)}$ as input and generates a modified demand power signal $MP_{DEMAND(t)}$, taking into account one or more other operating conditions then existing. The converter 112 receives $MP_{DEMAND(t)}$ as its input.

More particularly, the power down stage 94 monitors certain operating conditions of the electrode. The power down stage 94 compare the monitored conditions with preselected criteria for the second operating condition and generate an error signal when the second operating condition fails to meet the preselected criteria. In response to the error signal, the power down stage 94 modifies $P_{DEMAND(t)}$ in a non-linear fashion to set $MP_{DEMAND(t)}$ at a prescribed low demand power output value $P_{LOW}$. In the absence of the error signal, the power down stage 94 retains the value of $P_{DEMAND(t)}$ as the value of $MP_{DEMAND(t)}$.

The value of $P_{LOW}$ is selected to be above zero, but preferably below the power level at which tissue ablation occurs. In the illustrated and preferred embodiment, $P_{LOW}$ is about 1 watt.

The power down stage 94 sets the value of $MP_{DEMAND(t)}$ in a nonlinear fashion back to the value of $P_{DEMAND(t)}$ as soon as the operating conditions giving rise to the power down mode cease.

Figure 8:
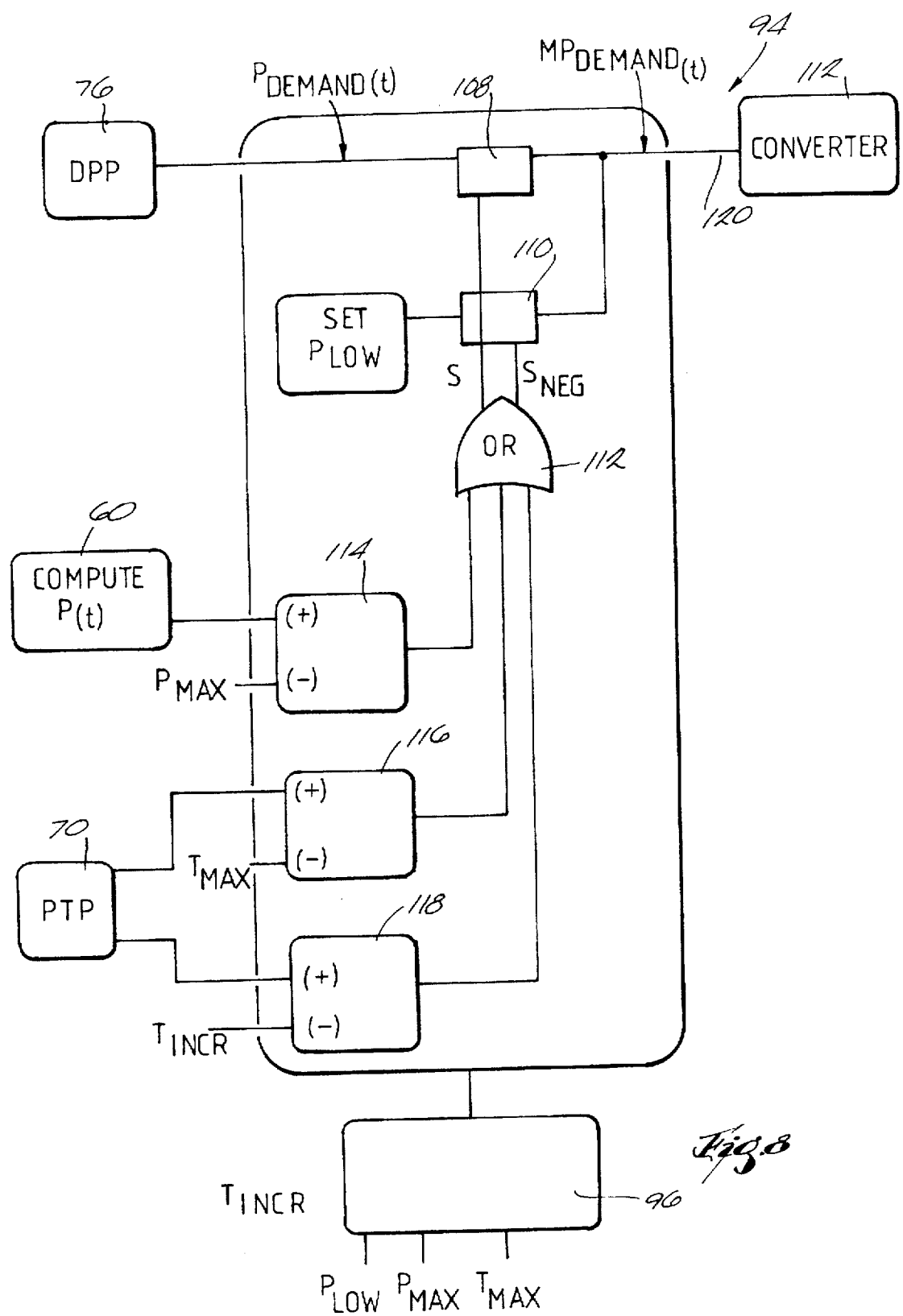
FIG. 8 is a schematic view of a system for use in association with the generator shown in FIG. 5 for scaling down power in response to prescribed power or temperature conditions.

In the illustrated and preferred embodiment, the power down stage 94 responds to prescribed power or temperature conditions. FIG. 8 schematically shows a preferred implementation of the power down stage 94.

The power down stage 94 includes microswitches 108 and 110. Microswitch 108 receives as input $P_{DEMAND(t)}$ from the DPP 76 (see FIG. 5, also). The microswitch 110 receives as input the value of $P_{LOW}$. An output line 114 connects the converter 112 in parallel to the outputs of the switches 108 and 110.

The power down stage also includes three comparators 114, 116, and 118. Each comparator 114, 116, and 118 independently controls the microswitches 108 and 110, taking into account different operating conditions.

In the illustrated and preferred embodiment (see FIG. 8), the outputs of the comparators 114, 116, and 118 are connected to OR gate 122. An output switch line S leads to the microswitch 108, while a negate switch line $S_{NEG}$ leads to microswitch 110. In the absence of any error signal from any comparator 114, 116, and 118 (when all operating conditions meet prescribed criteria), S=1 (closing switch 108) and $S_{NEG}$=0 (opening switch 110). In the presence of an error signal from any comparator 114, 116, and 118 (when at least one operating condition fails to meet prescribed criteria), S=0 (opening switch 108) and $S_{NEG}$=1 (closing switch 110).

(a) Based Upon Maximum Power Conditions

The output of the comparator 114 takes into account prescribed maximum power conditions. The comparator 114 receives current instantaneously power $P_{(t)}$ as its (+) input and a prescribed maximum power value $P_{MAX}$ as its inverse or (−) input.

In this implementation, the comparator 114 compares $P_{(t)}$ to the prescribed maximum power value $P_{MAX}$. An error free condition exists when $P_{(t)} < P_{MAX}$. In this condition, the comparator 114 sets microswitch 108 closed and microswitch 110 open. In this condition, the microswitch 108 passes through the value of $P_{DEMAND(t)}$ as the output $MP_{DEMAND(t)}$.

An error condition exists when $P_{(t)} \geq P_{MAX}$. In this condition, the comparator 114 sets the microswitch 108 open and microswitch 110 closed. In this condition, the microswitch 108 blocks passage of the value of $P_{DEMAND(t)}$, and $P_{LOW}$ becomes the output $MP_{DEMAND(t)}$. In effect, when $P_{(t)} > P_{MAX}$, the stage 94 reduces $P_{DEMAND(t)}$ to $P_{LOW}$ in an instantaneous, nonlinear fashion.

The value of $P_{MAX}$ can vary according to the particular requirements of the ablation procedure. The generator 12 can include, as part of its overall interface 13, an interface 96 for the physician to select and adjust $P_{MAX}$ (see FIG. 1 also). For cardiac ablation, it is believed that $P_{MAX}$ should lie in the range of about 50 watts to about 200 watts, with $P_{MAX}$ increasing as the surface area of the ablating electrode increases.

Figure 9:
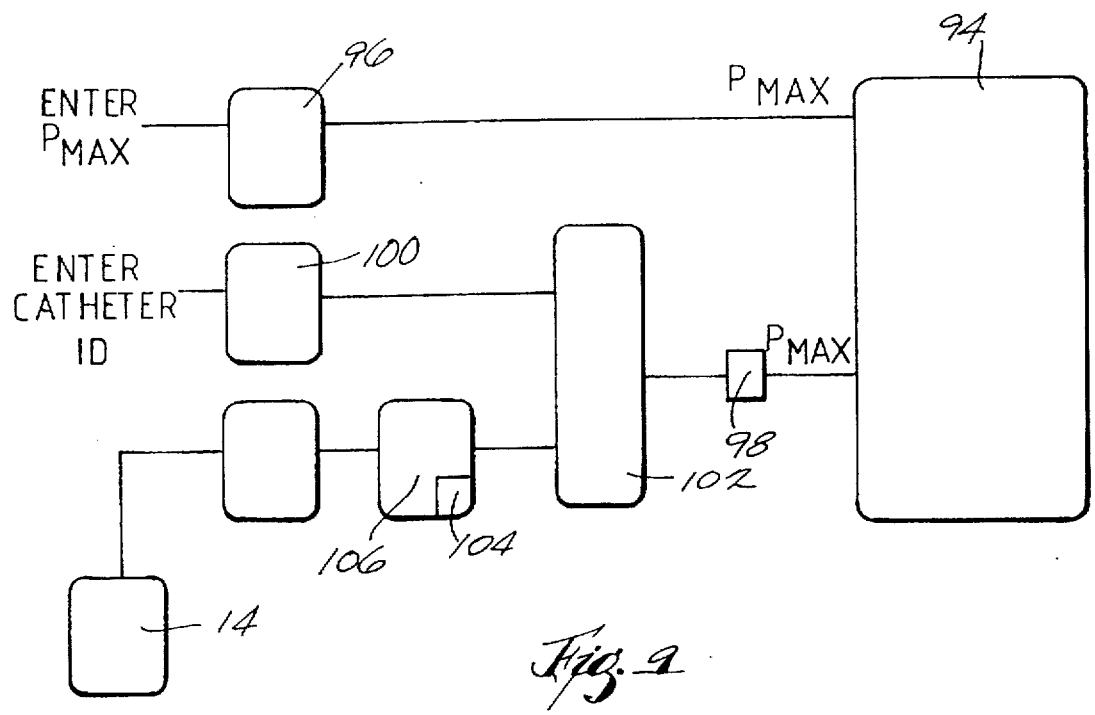
FIG. 9 is a schematic view of systems for use in association with the generator shown in FIG. 5 for establishing the maximum power condition for use by the scale back power system shown in FIG. 8.

As FIG. 9 shows, the value of $P_{MAX}$ can also be set, not upon direct power input settings by the physician, but rather upon the physical and/or functional characteristics of the ablating electrode being used, or both.

The physical and/or functional characteristics of the ablating electrode can include surface area, electrode configuration, electrode orientation, and electrode field dispersion properties. For example, an electrode with a smaller surface area can usually be expected to be operated at lower power settings.

The relationships among electrode type and $P_{MAX}$ can be determined by empirical testing. The test results can be transcribed in a look-up power criteria table 102 resident in ROM of the generator 12 (as FIG. 9 shows).

In the preferred embodiment, the power down stage 94A includes a register 98 for automatically setting $P_{MAX}$ based upon the power criteria transcribed in the look-up table 102.

The register 98 includes an input 100 (which is part of the overall interface 13 of the generator, as FIG. 1 also shows) for the physician to enter the electrode type being used. The register 98 then automatically sets $P_{MAX}$ in the second processing stage 58 based upon the power criteria table 102.

Alternatively (as FIG. 9 also shows), the catheter 14 can itself carry means for automatically producing an identification signal representing the electrode type when the catheter 14 is connected to the generator 12. The signal uniquely identifies the particular physical and/or performance characteristics of the connected electrode 16.

In this arrangement, a data acquisition element 106 queries and reads the identification signal of the catheter 14 to identify the electrode type. The element 106 then refers to the look-up table 102 to automatically set $P_{MAX}$ via the register 98.

The means for automatically generating the electrode-type identification signal can vary. FIG. 10 shows a preferred arrangement.

In the illustrated embodiment, the catheter handle 20 carries a resistor R having a prescribed ohm value. The ohm value of R represents the sum of calibration resistance value $R_{CAL}$ (as previously described) and a selected add-on resistance value $R_I$. The calibration resistance $R_{CAL}$ is a fixed value, depending upon the thermistor 34 the catheter 14 carries. The magnitude of the add-on value $R_I$ varies in predetermined increments depending upon the electrode type.

For example, a Type 1 Electrode is assigned an add-on value $R_I$ of 5000 ohms; a Type 2 Electrode is assigned an add-on value $R_I$ of 10,000 ohms; a Type 3 Electrode is assigned an add-on value $R_I$ of 15,000 ohms, and so on.

Assuming a fixed calibration resistance $R_C$ for the thermistor 34 used of 4000 ohms, the handle 20 for a Type 1 Electrode will carry a resistor R of 9000 ohms (4000 ohms calibration resistance $R_C$ plus 5000 ohms add-on resistance $R_I$); the handle 20 for a Type 2 Electrode will carry a resistor R of 14,000 ohms (4000 ohms calibration resistance $R_C$ plus 10,000 ohms add-on resistance $R_I$); and the handle 20 for a Type 3 Electrode will carry a resistor R of 19,000 ohms (4000 ohms calibration resistance $R_C$ plus 15,000 ohms add-on resistance $R_I$).

A look-up table 104 in the data acquisition element 106 (shown in FIG. 9) stores the fixed value $R_{CAL}$ of the calibration resistance, the range of add-on resistances $R_I$ corresponding to the identified electrode types, and their sum (which is the value of the resistor R that the system actually senses).

When connected to the generator 12 the element 106 senses the total ohm value of the resistor R in the handle 20. The element 106 refers to the look-up table 104. In the look-up table 104, a sensed total resistance R of less than 10,000 ohms identifies a Type 1 Electrode; a sensed total resistance R of 10,000 ohms to 15,000 ohms identifies a Type 2 Electrode; and a sensed total resistance R of over 15,000 ohms up to 20,000 ohms identifies a Type 3 Electrode.

The element 106 then refers to the power criteria look-up table 102 to obtain the corresponding power condition. The register 98 automatically sets $P_{MAX}$ in the power down stage 94A.

Referring still to the look-up table 104, the data acquisition element 106 subtracts the known add-on value for the identified Electrode Type. In this way, the generator 12 also derives the value of the calibration resistance $R_{CAL}$ for the thermistor 34. As already described (and as FIG. 5 shows), the first processing stage 56 processes the calibration resistance and the resistance sensed by the thermistor to derive the temperature $T_{M(t)}$, as previously described.

In an alternative embodiment (not shown), instead of the resistor R, the handle can carry a solid state micro-chip, ROM, EEROM, EPROM, or non-volatile RAM.

The micro-chip can be pre-programmed with digital values representing the calibration resistance for the thermistor 34 (or the calibration resistances for the multiple thermistors) and the appropriate value representing the Electrode Type. In this arrangement, the micro-chip outputs these values to the register 98, when queried by the data acquisition element 106.

(b) Based Upon Maximum Absolute Temperature Conditions

The output of the comparator 116 responds to prescribed maximum absolute temperature conditions. The comparator 116 receives at its (+) input the temperature value $T_{PRED(t)}$ from the PTP 70. The comparator 116 receives as its inverse or (−) input a prescribed maximum temperature value $T_{MAX}$.

In this implementation, the comparator 116 compares $T_{PRED(t)}$ to the prescribed maximum temperature value $T_{MAX}$. An error-free condition exists when $T_{PRED(t)} < T_{MAX}$. In this condition, the comparator 116 sets microswitch 108 closed and microswitch 110 open. In this condition, the microswitch 108 passes through the value of $P_{DEMAND(t)}$ as the output $MP_{DEMAND(t)}$.

An error condition exists when $T_{PRED(t)} \geq T_{MAX}$. In this condition, the comparator 116 sets the microswitch 108 open and microswitch 110 closed. In this condition, the microswitch 108 blocks passage of the value of $P_{DEMAND(t)}$, and $P_{LOW}$ becomes the output $MP_{DEMAND(t)}$. In effect, when $T_{PRED(t)} \geq T_{MAX}$, the stage 94 reduces $P_{DEMAND(t)}$ to $P_{LOW}$ in an instantaneous, nonlinear fashion.

The value of $T_{MAX}$ can be prescribed in various ways. It can, for example, be a selected absolute value that the physician inputs. For cardiac ablation, the value of $T_{MAX}$ is believed to lie in the range of 80° C. and 95° C., with a preferred representative value of about 90° C.

(c) Based Upon Incremental Temperature Conditions

The output of the comparator 118 responds to prescribed incremental temperature condition $T_{INCR}$ based upon $T_{SET}$ as follows:

$$T_{INCR} = T_{SET} + INCR$$

where INCR is a preselected increment.

The value of INCR can vary, just as $T_{SET}$ can vary, according to the judgment of the physician and empirical data. A representative value of INCR for cardiac ablation is believed to lie in the range of 2° C. to 8° C., with a preferred representative value of about 5° C.

The comparator 116, like the comparator 114, receives at its (+) input the temperature value $T_{PRED(t)}$ from the PTP 70. The comparator 116 receives as its inverse or (−) input the prescribed incremental temperature value $T_{INCR}$.

In this implementation, the comparator 116 compares $T_{PRED(t)}$ to the prescribed incremental temperature value $T_{INCR}$. An error-free condition exists when $T_{PRED(t)} < T_{INCR}$. In this condition, the comparator 116 sets microswitch 108 closed and microswitch 110 open. In this condition, the microswitch 108 passes through the value of $P_{DEMAND(t)}$ as the output $MP_{DEMAND(t)}$.

An error condition exists when $T_{PRED(t)} \geq T_{INCR}$. In this condition, the comparator 116 sets the microswitch 108 open and microswitch 110 closed. In this condition, the microswitch 108 blocks passage of the value of $P_{DEMAND(t)}$, and $P_{LOW}$ becomes the output $MP_{DEMAND(t)}$. In effect, when $T_{PRED(t)} \geq T_{INCR}$, the stage 94 reduces $P_{DEMAND(t)}$ to $P_{LOW}$ in an instantaneous, nonlinear fashion.

(d) Generating Demand Voltage

If any comparator 114, 116, or 118 opens switch 108 and closes switch 110 (i.e., when at least one error condition exists), $P_{LOW}$ is instantaneously set as $MP_{DEMAND(t)}$. Under this condition, the converter 112 receives $P_{LOW}$ as $MP_{DEMAND(t)}$. If none of the comparators 114, 116, or 118 opens switch 108 and closes switch 110, the converter 112 receives $P_{DEMAND(t)}$ as $MP_{DEMAND(t)}$.

The manner in which the converter 112 of the second processing stage 58 generates $V_{DEMAND(t)}$ to adjust $P_{(t)}$ can vary. For example, the converter 112 can employ proportional control principles, proportional integral derivative (PID) control principles, neural network, fuzzy logic, and adaptive control principles.

In one implementation, the converter 112 employs known PID principles to derive $V_{DEMAND}$. In this implementation, the converter 112 compares $MP_{DEMAND(t)}$ to the generated power signal $P_{(t)}$, which it receives from the multiplier 60. In this implementation, the converter 112 also takes into account the changes of the generated power signal $P_{(t)}$ over time. Based upon these considerations, the converter 112 of the second processing stage 58 derives the demand voltage signal $V_{DEMAND}$.

Alternatively, the converter 112 can use proportional control principles to directly convert $MP_{DEMAND(t)}$ to the demand voltage $V_{DEMAND(t)}$, as follows:

$$V_{DEMAND(t)} = \sqrt{MP_{DEMAND(t)} Z_{(t)}}$$

where $Z_{(t)}$ is the sensed impedance of the system and $V_{DEMAND(t)}$ is the RMS value of the output voltage.

(e) Monitoring Impedance

For this and other purposes, the generator 12 preferably includes an impedance microprocessor 88. The impedance microprocessor 88 receives the instantaneous current signal $I_{(t)}$ and the instantaneous voltage signal $V_{(t)}$ from the sensing transformers 62 and 64, already described. The microprocessor 88 derives impedance $Z_{(t)}$ (in ohms) as follows:

$$Z_{(t)} = \frac{V_{(t)}}{I_{(t)}}$$

Preferably, the generator 12 includes a display 90 as part of its overall interface 13 to show the measured impedance $Z_{(t)}$ (see FIG. 1 also).

The microprocessor 88 also preferably maintains a record of sampled impedances $Z_{(t)}$ over time. From this, the microprocessor calculates the changes in impedance during a selected interval and generates appropriate control signals based upon predetermined criteria. Even when the power down stage 94 sets $P_{DEMAND(t)}$ as $P_{LOW}$ to stop tissue ablation, the microprocessor still serves to continuously compute $Z_{(t)}$ for the purposes set forth below.

For example, if measured impedance falls outside a predetermined set range, the microprocessor 88 generates a command signal to shut off power to the ablation electrode 16. The set range for impedance for a cardiac ablation procedure is believed to be about 50 to 300 ohms.

When impedance begins in the set range and, over time, increases beyond it, the most likely cause is coagulum formation on the ablation electrode 16. A sudden rise in impedance over the set range suggests the sudden onset of coagulum formation or a sudden shift in the position of the ablation electrode 16. Rapid fluctuations of the impedance also could suggest poor contact between the ablation electrode 16 and the targeted tissue. All require prompt response; for example, withdrawal and cleaning of the ablation electrode 16, or repositioning of the ablation electrode 16.

The generator 12 preferably includes visual and auditory alarms 92 as part of its overall interface 13 (see FIG. 1 also), to transmit a warning to the user when these impedance-related conditions occur.

A very high impedance value could suggest poor skin contact with the indifferent electrode 18, or an electrical problem in the generator 12. Again, this calls for prompt corrective action.

(f) Error Shutdown Mode The power down stage 94 rapidly reduces but does not shut down power, based upon prescribed instantaneous high power or high temperature conditions. In the illustrated and preferred embodiment, the second processing stage 58 also includes an error shutdown stage 128. The error shutdown stage 128 responds to the persistence, over a set time period, of a prescribed over-temperature condition or conditions indicative of an actual or developing system failure. The error shutdown phase 126 turns off all power to the electrode 16. The error shutdown phase 128 can work separately from or in tandem with the power down mode.

For example, as long as $T_{PRED(t)}$ exceeds $T_{SET}$ by an amount less than INCR, the power down stage 94C will not be triggered to set $P_{LOW}$. Still, if this over-temperature situation persists for more than a prescribed period of time (for example, 2 to 5 seconds), the second processing stage 58 can be conditioned to assume an actual or developing system failure, and institute a power shutdown.

By way of another example, if $T_{PRED(t)} \geq T_{MAX}$ or $T_{INCR}$, the power down stage 94B or C will be triggered to set $P_{LOW}$. If this over-temperature situation persists during the power down conditions for a prescribed period of time (for example, 2 to 5 seconds), the second processing stage 58 can be conditioned to assume an actual or developing system failure, and institute a power shutdown.

The generator 12 as described provides control over the ablation procedure. The monitoring and control of power assure the effective distribution of radio frequency energy to the ablation electrode 16, while setting safe physiological limits.

The generator 12 can also include an alternative control mode based upon power. In this mode, the generator 12 seeks to maintain a set power condition, independent of measured temperature conditions. The generator 12 would switch to the power control mode, for example, when the electrode 16 in use does not carry a temperature sensing element 30, or upon selection by the physician, even when the electrode 16 has a temperature sensing element 30.

The illustrated and preferred embodiments envision the use of micro-processor controlled components using digital processing to analyze information and generate feedback signals. It should be appreciated that other logic control circuits using micro-switches, AND/OR gates, invertors, and the like are equivalent to the micro-processor controlled components and techniques shown in the preferred embodiments.

Various features of the invention are set forth in the claims that follow.

We claim:

1. An apparatus for ablating heart tissue with energy from an energy source, the apparatus comprising an electrode for emitting energy from the energy source to ablate body tissue;

a sensing element for measuring temperature at the electrode; and a controller coupled to the electrode and the sensing element, the controller including memory means for storing a temperature set curve including a first region of temperature values established over a first time period of at least one second that are below tissue ablating temperatures and a second region of temperature values at tissue ablation temperatures established over a second time period of at least one second and after the first time period, data acquisition means, coupled to the sensing element, for deriving temperature information at the energy emitting electrode during the first and second time periods based upon temperature measured by the sensing element, and processing means, coupled to the memory element and the data acquisition means, for generating (i) a first output signal based upon comparing temperature information derived during the first time period to the first region of temperature values stored in the memory means and (ii) a second output signal based upon comparing temperature information derived during the second time period to the second region of temperature values stored in the memory means, and output means, coupled to the processing means and to the energy source, for varying energy supplied by the energy source to the electrode in response to the first and second output signals to establish and maintain temperature at the electrode over time approximately along the temperature set curve.

2. An apparatus as claimed in claim 1, wherein the first time period is between approximately one second and approximately seven seconds.

3. An apparatus as claimed in claim 1, wherein the second time period is at least two seconds.

4. An apparatus as claimed in claim 1, wherein the controller further comprises second processing means for determining a temperature beneath the surface of the tissue.

5. An apparatus as claimed in claim 1, wherein the controller further comprises second processing means for determining whether an overtemperature condition persists for more than a predetermined period and power shutdown means for instituting a power shutdown in response to a determination that an overtemperature condition has existed for more than the predetermined period.

6. An apparatus as claimed in claim 1, wherein the first region includes temperature values in the range of 45° C. to 50° C.

7. An apparatus as claimed in claim 1, wherein the second region includes temperature values in the range of 50° C. to 90° C.

8. An apparatus for ablating heart tissue with energy from an energy source, the apparatus comprising an electrode for emitting energy from the energy source to ablate body tissue, a sensing element for measuring temperature at the electrode, a controller coupled to the electrode and the sensing element and operable to provide both a diagnostic function and a therapeutic function comprising a memory element to store a temperature set curve including a first region of temperature values established over a first time period of at least one second that are below tissue ablating temperatures to allow diagnostic thermal mapping of heart tissue during the first time period and a second region of temperature values at tissue ablation temperatures established over a second time period of at least one second and after the first time period to allow therapeutic tissue ablation during the second time period, a data acquisition element coupled to the sensing element to derive temperature information at the energy emitting electrode during the first and second time periods based upon temperature measured by the sensing element, and a processing element coupled to the memory element and the data acquisition element receiving derived temperature information from the data acquisition element to generate (i) a first output signal based upon comparing temperature information derived during the first time period to the first region of temperature values stored in the memory element and (ii) a second output signal based upon comparing temperature information derived during the second time period to the second region of temperature values stored in the memory element, and an output element coupled to the processing element and to the energy source to vary energy supplied by the energy source to the electrode in response to the first and second output signals to establish and maintain temperature at the electrode over time approximately along the temperature set curve.

9. An apparatus according to claim 8 wherein the first region includes temperature values in the range of 45° C. to 50° C.

10. An apparatus according to claim 8 wherein the second region includes temperature values in the range of 50° C. to 90° C.

11. An apparatus as claimed in claim 8, wherein the first time period is between approximately one second and approximately seven seconds.

12. An apparatus as claimed in claim 8, wherein the second time period is at least two seconds.

13. An apparatus as claimed in claim 8, wherein the controller further comprises a second processing element for determining a temperature beneath the surface of the tissue.

14. An apparatus as claimed in claim 8, wherein the controller further comprises a second processing element for determining whether an overtemperature condition persists for more than a predetermined period and a power shutdown element for instituting a power shutdown in response to a determination that an overtemperature condition has existed for more than the predetermined period.

15. A method for ablating heart tissue comprising the steps of establishing a temperature set curve for ablating tissue including a first region of temperature values established over a first time period of at least one second that are below tissue ablating temperatures to allow thermal mapping and a second region of temperature values at tissue ablation temperatures established over a second time period of at lest one second and after the first time period, supply ablating energy to an electrode, deriving diagnostic temperature information by sensing temperature at the electrode during the first time period, deriving therapeutic temperature information by sensing temperature at the electrode during the second time period, and controlling the supply of ablating energy to the electrode based, at least in part, upon comparing the diagnostic and therapeutic temperature information derived during the first and second time periods to the respective first and second regions of temperature values to establish and maintain temperature at the electrode over time approximately along the temperature set curve.

16. A method according to claim 15 wherein the first region includes temperature values in the range of 45° C. to 50° C.

17. A method according to claim 15 wherein the second region includes temperature values in the range of 50° C. to 90° C.

18. A method as claimed in claim 15, wherein the first time period is between approximately one second and approximately seven seconds.

19. A method as claimed in claim 15, wherein the second time period is at least two seconds.

20. A method as claimed in claim 15, wherein the step of deriving therapeutic temperature information comprises determining a temperature beneath the surface of the tissue.

21. A method as claimed in claim 15, wherein the step of controlling the supply of ablation energy comprises determining whether an overtemperature condition persists for more than a predetermined period and instituting a power shutdown in response to a determination that an overtemperature condition has existed for more than the predetermined period.

* * * * *